United States Patent [19]
Long et al.

[11] Patent Number: 5,624,429
[45] Date of Patent: Apr. 29, 1997

[54] MECHANICAL FASTENING SYSTEM WITH GRIP TAB

[75] Inventors: Andrew M. Long; Andrew E. Huntoon; Sang V. Tran; Lori A. Roocks, all of Appleton; Patrick R. Lord, Neenah; Gordon A. Shaw, Greenville, all of Wis.

[73] Assignee: Kimberly-Clark Corporation, Neenah, Wis.

[21] Appl. No.: 603,477

[22] Filed: Mar. 6, 1996

[51] Int. Cl.⁶ .................................................. A61F 13/15
[52] U.S. Cl. .................. 604/391; 24/306; 24/DIG. 11; 2/912; 2/913; 2/914; 2/915
[58] Field of Search .................. 2/912, 913, 914, 2/915; 24/306, DIG. 11; 604/389–391

[56] References Cited

U.S. PATENT DOCUMENTS

| | | | |
|---|---|---|---|
| 2,738,789 | 3/1956 | Foxworthy | 128/167 |
| 2,834,347 | 5/1958 | Connally | 128/284 |
| 3,089,494 | 5/1963 | Schwartz | 128/284 |
| 3,221,738 | 12/1965 | Ekberg et al. | 128/287 |
| 3,620,217 | 11/1971 | Gellert | 128/284 |
| 3,800,796 | 4/1974 | Jacob | 128/284 |
| 3,901,236 | 8/1975 | Assarsson et al. | 128/284 |
| 3,948,258 | 4/1976 | Karami | 128/287 |
| 3,948,267 | 4/1976 | Karami | 128/287 |
| 3,950,824 | 4/1976 | Karami | 24/67 AR |
| 3,967,624 | 7/1976 | Milnamow | 128/287 |
| 4,010,753 | 3/1977 | Tritsch | 128/284 |
| 4,034,752 | 7/1977 | Tritsch | 128/184 |
| 4,051,853 | 10/1977 | Egan, Jr. | 128/287 |
| 4,060,085 | 11/1977 | Karami | 128/287 |
| 4,063,559 | 12/1977 | Tritsch | 128/287 |
| 4,066,081 | 1/1978 | Schaar | 128/287 |
| 4,074,716 | 2/1978 | Schaar | 128/287 |
| 4,076,663 | 2/1978 | Masuda et al. | 260/17.4 GC |
| 4,090,516 | 5/1978 | Schaar | 128/287 |
| 4,158,363 | 6/1979 | Schaar | 128/287 |
| 4,186,744 | 2/1980 | Ness | 128/287 |
| 4,209,016 | 6/1980 | Schaar | 128/287 |
| 4,237,889 | 12/1980 | Gobran | 128/287 |
| 4,286,082 | 8/1981 | Tsubakimoto et al. | 526/240 |
| 4,299,223 | 11/1981 | Cronkrite | 128/287 |
| 4,389,212 | 6/1983 | Tritsch | 604/389 |
| 4,500,316 | 2/1985 | Damico | 604/389 |
| 4,556,595 | 12/1985 | Ochi | 428/143 |
| 4,646,397 | 3/1987 | Yoshida | 24/442 |
| 4,655,761 | 4/1987 | Grube et al. | 604/389 |
| 4,662,037 | 5/1987 | Provost et al. | 24/447 |
| 4,663,220 | 5/1987 | Wisneski et al. | 428/221 |
| 4,672,722 | 6/1987 | Malamed | 24/446 |
| 4,699,823 | 10/1987 | Kellenberger et al. | 428/219 |
| 4,701,170 | 10/1987 | Wilson et al. | 604/385 A |

(List continued on next page.)

FOREIGN PATENT DOCUMENTS

| | | |
|---|---|---|
| 0217032A3 | 4/1987 | European Pat. Off. . |
| 0264959A2 | 4/1988 | European Pat. Off. . |
| 0233704B1 | 7/1992 | European Pat. Off. . |
| 63-309606 | 12/1988 | Japan . |
| 1426147 | 3/1974 | United Kingdom . |
| 2249469 | 5/1992 | United Kingdom . |
| 2277867 | 11/1994 | United Kingdom . |
| 2277865 | 11/1994 | United Kingdom . |
| 94/17768 | 8/1994 | WIPO . |

*Primary Examiner*—Robert A. Clarke
*Attorney, Agent, or Firm*—Paul Yee

[57] ABSTRACT

A distinctive article can include an elastomerically stretchable side panel having a longitudinal dimension and a lateral dimension. A member of hook material is operably connected to a first, laterally outboard edge portion of the side panel, and each member of hook material includes a hook base layer which has an appointed fastening region and an appointed grip region. The fastening region has a plurality of hook elements which are integrally formed with the base layer and extend away from a base plane of the hook base layer. The hook elements are configured to operably engage a selected, cooperating loop material. The grip region has a relatively lower density of the hook elements per unit area, as compared to the fastening region. The fastening region is interposed between the side panel and the grip region. The grip region provides a laterally terminal edge of the article.

31 Claims, 5 Drawing Sheets

U.S. PATENT DOCUMENTS

| | | | |
|---|---|---|---|
| 4,701,176 | 10/1987 | Wilson et al. | 604/385 A |
| 4,704,115 | 11/1987 | Buell | 604/385 A |
| 4,704,116 | 11/1987 | Enloe | 604/385 A |
| 4,743,242 | 5/1988 | Grube et al. | 604/389 |
| 4,753,646 | 6/1988 | Enloe | 604/385 R |
| 4,753,648 | 6/1988 | Jackson | 604/389 |
| 4,753,649 | 6/1988 | Pazdernik | 604/389 |
| 4,773,906 | 9/1988 | Krushel | 604/391 |
| 4,787,897 | 11/1988 | Torimae et al. | 604/389 |
| 4,795,510 | 1/1989 | Wittrock et al. | 156/64 |
| 4,820,296 | 4/1989 | Masliyah | 604/385.1 |
| 4,826,499 | 5/1989 | Ahr | 604/389 |
| 4,834,742 | 5/1989 | Wilson et al. | 604/389 |
| 4,842,596 | 6/1989 | Kielpikowski et al. | 604/385.2 |
| 4,850,988 | 7/1989 | Aledo et al. | 604/385.1 |
| 4,883,481 | 11/1989 | Blanchard | 604/385.1 |
| 4,887,339 | 12/1989 | Bellanger | 24/575 |
| 4,894,060 | 1/1990 | Nestegard | 604/391 |
| 4,895,569 | 1/1990 | Wilson et al. | 604/386 |
| 4,911,702 | 3/1990 | O'Leary et al. | 604/389 |
| 4,916,005 | 4/1990 | Lippert et al. | 428/192 |
| 4,938,753 | 7/1990 | Van Gompel et al. | 604/385.2 |
| 4,955,113 | 9/1990 | Rajala et al. | 24/448 |
| 4,984,339 | 1/1991 | Provost et al. | 24/452 |
| 5,019,073 | 5/1991 | Roessler et al. | 604/391 |
| 5,024,672 | 6/1991 | Widlund | 604/390 |
| 5,040,525 | 8/1991 | Georgijevic | 128/78 |
| 5,092,862 | 3/1992 | Muckenfuhs et al. | 604/385.2 |
| 5,141,790 | 8/1992 | Calhoun et al. | 428/40 |
| 5,147,347 | 9/1992 | Huang et al. | 604/390 |
| 5,158,557 | 10/1992 | Noreen et al. | 604/389 |
| 5,170,505 | 12/1992 | Rohrer | 2/69 |
| 5,226,992 | 7/1993 | Morman | 156/62.4 |
| 5,242,436 | 9/1993 | Weil et al. | 604/385.2 |
| 5,269,776 | 12/1993 | Lancaster et al. | 604/387 |
| 5,279,604 | 1/1994 | Robertson et al. | 604/389 |
| 5,386,595 | 2/1995 | Kuen et al. | 2/400 |
| 5,399,219 | 3/1995 | Roessler et al. | 156/259 |
| 5,401,275 | 3/1995 | Flug et al. | 604/391 |
| 5,407,439 | 4/1995 | Goulait | 604/391- |

MECHANICAL FASTENING SYSTEM WITH GRIP TAB

FIELD OF THE INVENTION

The present invention relates to fastening systems for garments and other articles. More particularly, the present invention relates to adhesive tape fastening systems and interlocking, mechanical-type fastening systems which can be employed with disposable articles, such as gowns, diapers, incontinence garments and the like.

BACKGROUND OF THE INVENTION

Conventional disposable absorbent articles have typically employed adhesive fastening tapes for securing the article on a wearer. Such articles have also been constructed with interengaging mechanical fasteners, such as VELCRO brand hook-and-loop fasteners. Particular articles have included a fastening system which extends along substantially the entire length of an ear section of the article. Other fastening systems have included strips or segmented sections of adhesive. Still other systems have employed tapered fastening tabs where the adhesive area on the user's end is relatively wide at the longitudinally extending sides of the diaper, and is tapered to a more narrow width at its distal end. For example, see European patent EP 0 233 704 B1 of H. Burkhard et al.

Conventional fastening systems, such as those described above, have not provided an adequate level of dynamic fit in combination with a neat tailored appearance and reliable securement. The conventional fastening systems have not provided a sufficient capability to accommodate the stresses imposed by fastening the article on a wearer, while also accommodating the other stresses and displacements caused by a moving wearer. As a result, the fastening systems have not provided desired levels of comfort, securement and ease of manufacture.

BRIEF DESCRIPTION OF THE INVENTION

Generally stated, the present invention provides a distinctive article which includes a side panel having a longitudinal dimension and a lateral dimension. A first mechanical fastening component is operably connected to a first, laterally outboard edge portion of the side panel, and the first mechanical fastening component includes a base layer which has an appointed fastening region and an appointed grip region. The fastening region has a plurality of first mechanical fastening elements which are integrally formed with the base layer and extend away from a base plane of the base layer, and the first mechanical fastening elements are configured to operably engage a cooperating, second mechanical fastening component. The grip region has a relatively lower density of the first mechanical fastening elements as compared to the fastening region. The fastening region is interposed between the side panel and the grip region, and the grip region provides a laterally terminal edge of the article.

The various aspects of the fastening system of the invention can provide improved securement with greater resistance to premature pop-opens, and can also provide improved fit, greater comfort, reduced irritation of the wearers skin. A grip tab region of the fastening system can be configured with a relatively high stiffness to help produce a desired close association, which can better maintain a position which lies substantially flat against an appointed, fastener landing zone of the article.

BRIEF DESCRIPTION OF THE DRAWINGS

The present invention will be more fully understood and further advantages will become apparent when reference is made to the following detailed description of the invention and the drawings, in which.

DETAILED DESCRIPTION OF THE INVENTION

The various embodiments of the invention will be described in the context of a disposable absorbent article, such as a disposable diaper. It is, however, readily apparent that the present invention could also be employed with other articles, such as caps, gowns, shoe covers, feminine care articles, incontinence garments and the like, which may be configured to be disposable. Typically, disposable articles are intended for limited use and are not intended to be laundered or otherwise cleaned for reuse. A disposable diaper, for example, is discarded after it has become soiled by the wearer. In the context of the present invention, a mechanical fastening system is a system which includes cooperating components which mechanically inter-engage to provide a desired securement.

With reference to FIGS. 1, 2, 3 and 4, an article, such as the representatively shown disposable diaper 20, can include a side panel 90 having a longitudinal dimension 86 and a lateral dimension 88. A first mechanical fastening component is operably connected to a first, laterally outboard edge portion 92 of the side panel 90, and the first mechanical fastening component includes a base layer, such as a hook base layer 48, which has an appointed fastening region 50 and an appointed grip region 52. The fastening region has a plurality of first mechanical fastening elements, such as hook elements 54, which are integrally formed with the base layer and extend away from a base plane which is generally defined by the base layer. The first mechanical fastening elements are configured to operably engage a cooperating, second mechanical fastening component, such as a loop material 80, which can be positioned on a selected landing zone 78 (FIG. 2) of the article. The grip region 52 has a relatively lower density of the first mechanical fastening elements per unit area, as compared to the fastening region 50. In addition, the fastening region 50 is interposed between the side panel 90 and the grip region 52, and the grip region provides a laterally terminal edge 64 of the article.

In the representatively shown arrangement, the first mechanical fastening component is provided by a member of hook material 46 which is operably connected to a first, laterally outboard edge portion 92 of the side panel. Each member of hook material includes a hook base layer 48 which has an appointed fastening region 50 and an appointed grip region 52. The fastening region 50 has a plurality of hook elements 54 which are integrally formed with the base layer 48 and which extend away from the base plane which is generally defined by the base layer. The hook elements 54 are configured to operably engage a selected, cooperating loop material 80. The grip region 52 has a relatively lower density of the hook elements 54 per unit area, as compared to the fastening region 50. The fastening region 50 is interposed between the side panel 90 and the grip region 52, and the grip region provides a laterally terminal edge of the article 20. It should be readily appreciated, however, that the locations of the hook material and the loop material may optionally be reversed. Accordingly, a member of loop material 80 could operably be connected to a first, laterally outboard edge portion 92 of the side panel, and a section of hook material could operably be located at the desired landing zone of the article.

The shown configuration also illustrates a composite assembly which includes a side panel 90 and its associated member of hook material 46, and which is attached to each side edge region of a selected waistband section of the article. In particular, a composite assembly 72 is shown attached to side edge regions 116 of a rear waistband section 40.

In a particular aspect of the invention, each composite assembly 72 can include a carrier layer 56 which has a first side region 58 and a second side region 60. In the shown arrangement, the carrier layer interconnects between the side panel 90 and the member of hook material 46. The member of hook material is affixed to the first carrier side region 58, and the second carrier side region 60 is attached to the outboard edge portion 92 of the side panel 90.

A particular aspect of the invention can further provide an absorbent article, such as an absorbent disposable diaper 20. For example, the diaper can include a backsheet layer 22, a liquid permeable topsheet layer 24 connected and integrated with the backsheet layer, and an absorbent structure, such as absorbent body 26, which is sandwiched between the backsheet and topsheet layers.

Figure 1:
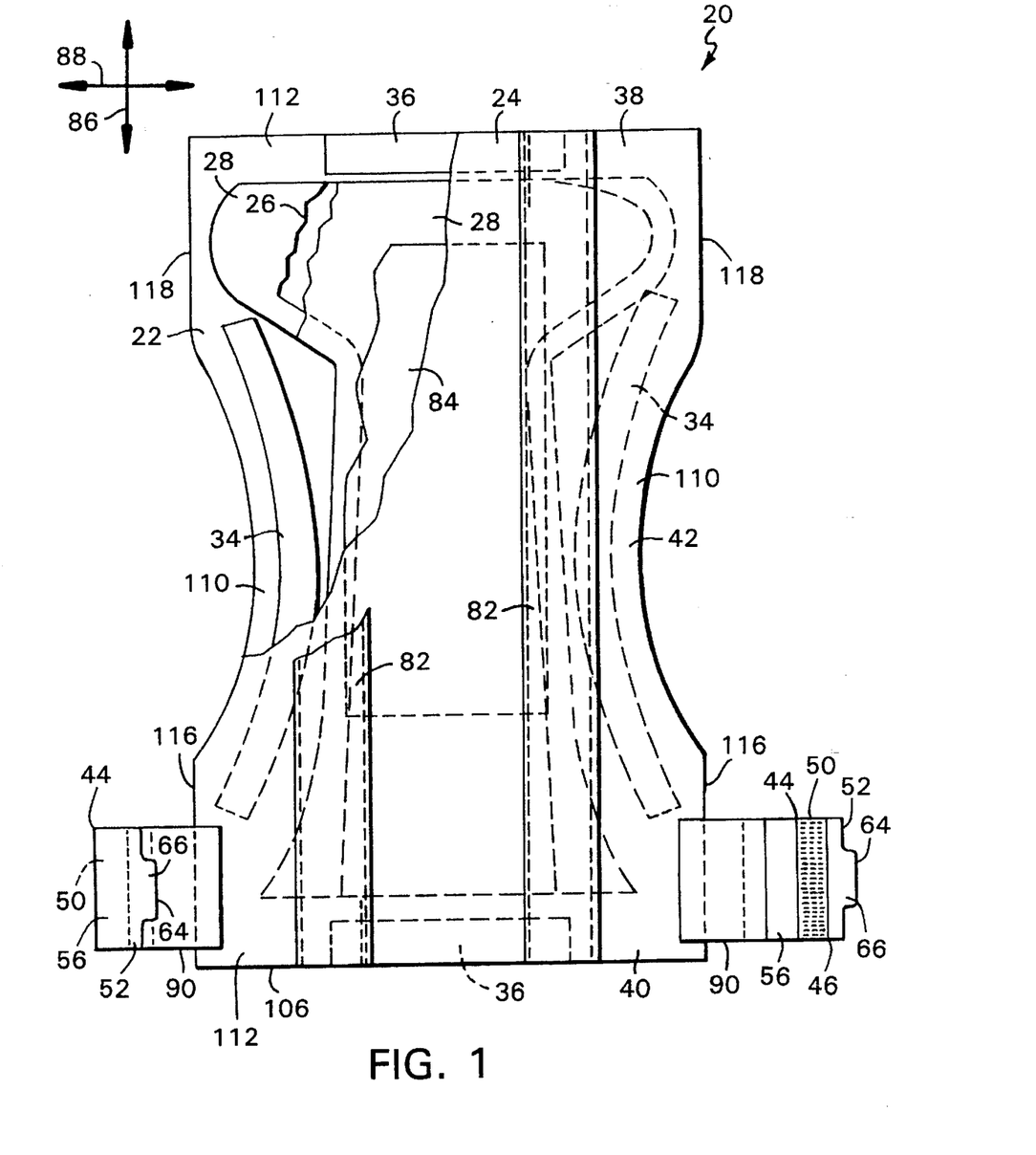
FIG. 1 representatively shows a partially cut-away, top view of a diaper article which incorporates the fastening system of the invention.
Figure 2:
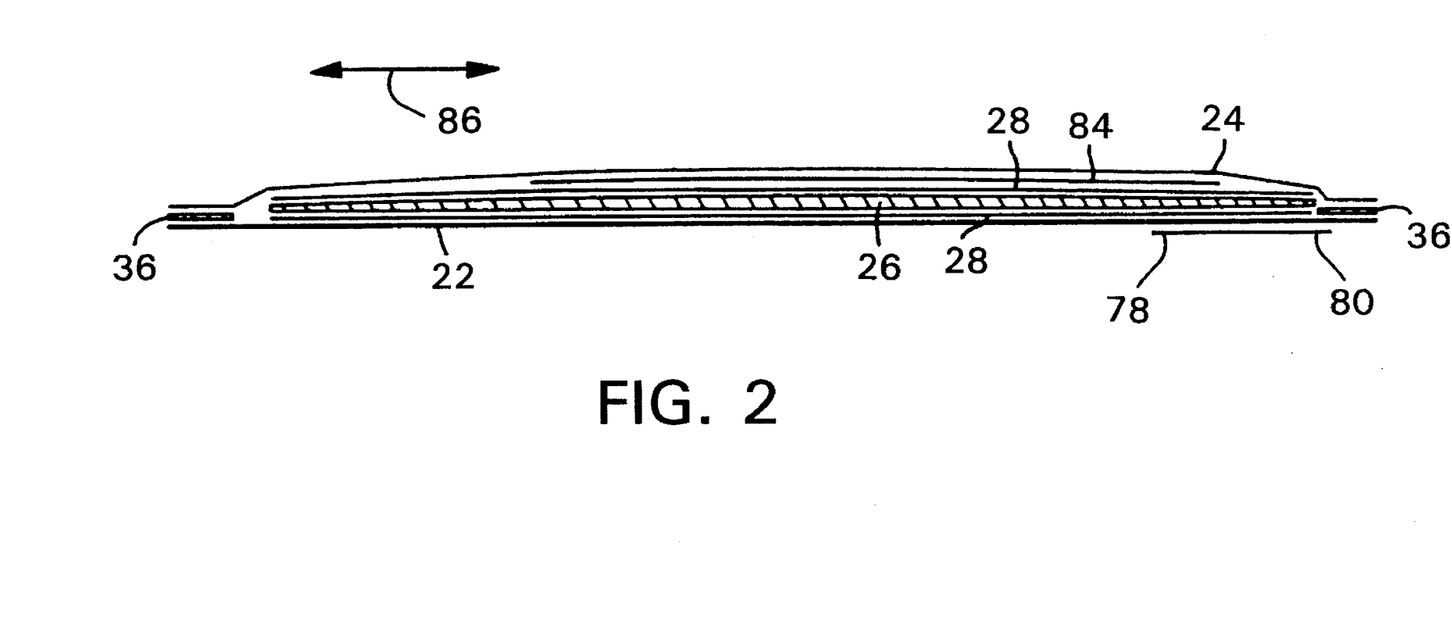
FIG. 2 representatively shows a schematic, longitudinal cross-sectional view of the article illustrated in FIG. 1.
Figure 3:
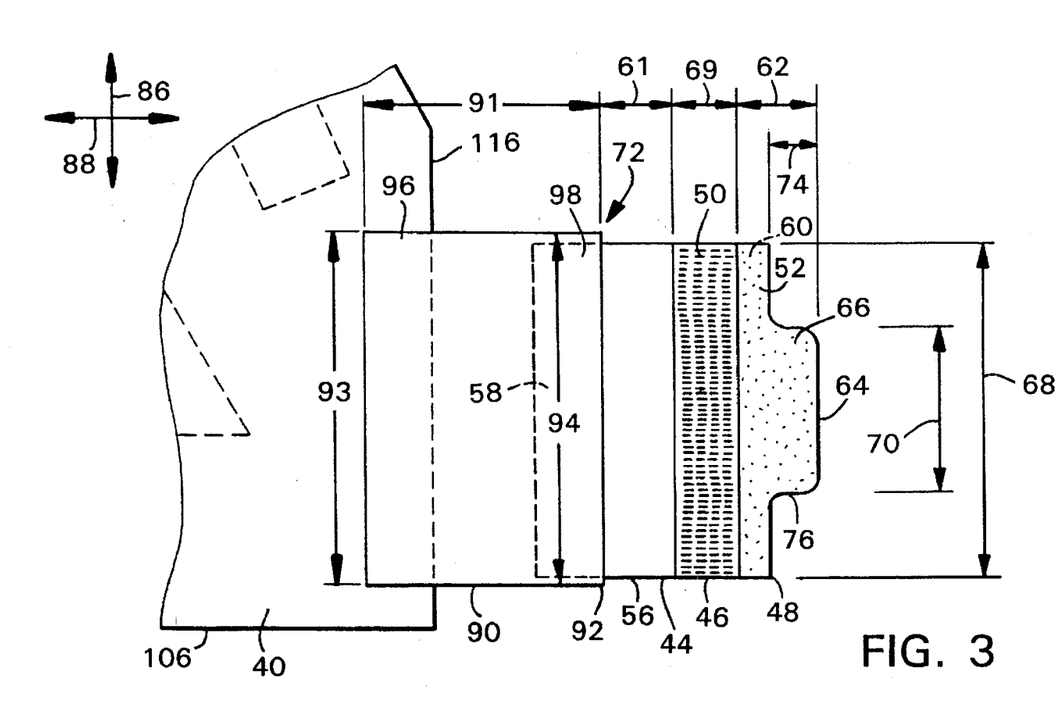
FIG. 3 representatively shows a top view of a side panel and fastening tab assembly of the invention.

With reference to FIGS. 1, 2 and 3, a further aspect of the invention provides an absorbent article, such as diaper 20, having a longitudinal dimension 86, a lateral, cross-wise dimension 88, a front waistband section 38 with a laterally opposed, front pair of side edge regions 118, a rear waistband section 40 with a laterally opposed, rear pair of side edge regions, 116, and an intermediate section 42 which interconnects the front and rear waistband section. The article includes a backsheet layer 22 having an appointed fastener landing zone 78 disposed on an outward surface of the backsheet layer. A liquid permeable topsheet layer 24 is superposed in facing relation with the backsheet layer 22, and an absorbent body 26 is sandwiched between the backsheet layer 22 and topsheet layer 24. A side panel 90, such as an elastomerically stretchable side panel, is attached to each side edge region of one of the waistband sections of the article. In the shown arrangement, the side panels 90 are attached to each laterally opposed side edge region 116 of the rear waistband section 40. A member of a first mechanical fastening component, such as a member of hook material 46, is operably connected to a first, laterally outboard edge portion 92 of each side panel 90. Each member of hook material 46 includes a base layer, such as the hook base layer 48, which has an appointed fastening region 50 and an appointed grip region 52. The fastening region 50 has a plurality of first fastening elements, such as hook elements 54, which are integrally formed with the base layer and extend away from a base plane which is generally defined by the base layer 48. The first fastening elements are configured to operably engage a second mechanical fastening component, such as the appointed loop material 80, to secure the article on a wearer. The grip region 52 has a relatively lower density of the hook elements 54 per unit area, as compared to the fastening region 50. The fastening region 50 is interposed between the side panel 90 and the grip region 52, and the grip region 52 provides a laterally terminal edge 64 of the article.

The illustrated configuration, the member of the first mechanical fastening component, such as the member of hook material 46, is provided by a composite fastener tab 44 which includes a carrier layer member 56. A fastener tab is affixed to each of the side panels 90 located at laterally opposed, side edge regions 116 of the rear waistband section 40 of the article. The fastener tab at one side region 116 has a similar, mirror-image configuration and construction, as compared to the opposite fastener tab.

The fastening system provided by the present invention can advantageously reduce the occurrence of pop-opens and provide a more reliable securement by providing for a mechanical engagement along a fastening region 52 which has a relatively large size along the longitudinal dimension 86. In addition, the relatively high stiffness value of the grip region 52, particularly at a grip tab 66, can reduce undesired pop-opens, and other unintended or nuisance openings by the wearer. The additional presence of a supplemental fastening region 100 (FIGS. 5 through 7) can further reduce pop-opens, as well as other undesired or premature openings.

FIG. 1 is a representative plan view of the representative disposable diaper 20 of the present invention in its flat-out, uncontracted state (i.e., with substantially all elastic induced gathering and contraction removed). Portions of the structure are partially cut away to more clearly show the interior construction of the diaper article, and the bodyside surface of the diaper which contacts the wearer is facing the viewer. The outer edges of the diaper define a periphery with longitudinally extending side edge margins 110 and laterally extending end edge margins 112. The side edges define leg openings for the diaper, and optionally, are curvilinear and contoured. The end edges are shown as straight, but optionally, may be curvilinear. The article has a first waistband section, such as rear waistband section 40, a second waistband section, such as front waistband section 38, and an intermediate section 42 which interconnects the first and second waistband sections.

The diaper 20 typically includes a porous, liquid permeable topsheet 24; a substantially liquid impermeable backsheet 22; an absorbent structure 26, positioned and connected between the topsheet and backsheet; a surge management portion 84; and elastic members, such as leg elastics 34 and waist elastics 36. The surge management portion is positioned in a liquid communication with a retention portion of the absorbent structure, and the topsheet 24, backsheet 22, absorbent structure 26, surge management portion 84 and elastic members 34 and 36 may be assembled together into a variety of well-known diaper configurations. The diaper can additionally include a system of containment flaps 82, and side panel members 90.

Examples of articles which include elasticized side panels and selectively configured fastener tabs are described in U.S.

patent application Ser. No. 168,615 of T. Roessler et al., entitled DYNAMIC FITTING DIAPER, and filed Dec. 16, 1993 (attorney docket No. 10,961). Various techniques for forming the desired fastening systems are described in U.S. Pat. No. 5,399,219 of T. Roessler et al., entitled METHOD FOR MAKING A FASTENING SYSTEM FOR A DYNAMIC FITTING DIAPER and issued Mar. 21, 1995 (attorney docket No. 11,186); in U.S. patent application Ser. No. 286,086 of D. Fries, entitled A PROCESS FOR ASSEMBLING ELASTICIZED EAR PORTIONS and filed Aug. 3, 1994 (attorney docket No. 11,169); and in U.S. patent application Ser. No. 08/415,383 of D. Fries, entitled AN ASSEMBLY PROCESS FOR A LAMINATED TAPE and filed Apr. 3, 1995 (attorney docket No. 11,950). The disclosures of the above-described documents are incorporated herein by reference in a manner that is consistent (not in conflict) herewith.

Diaper 20 generally defines a longitudinally extending length dimension 86 and a laterally extending width dimension 88, as representatively shown in FIG. 1, and may have any desired shape, such as rectangular, I-shaped, a generally hourglass shape, or a T-shape. With the T-shape, the crossbar of the "T" may comprise the front waistband portion of the diaper, or may alternatively comprise the rear waistband portion of the diaper.

The topsheet 24 and backsheet 22 may be generally coextensive, and may have length and width dimensions which are generally larger than and extend beyond the corresponding dimensions of absorbent structure 26 to provide for corresponding portions of the side and end margins. Topsheet 24 is associated with and superimposed on backsheet 22, thereby defining the periphery of the diaper 20. The waistband regions comprise those portions of the diaper, which when worn, wholly or partially cover or encircle the waist or mid-lower torso of the wearer. The intermediate, crotch region 42 lies between and interconnects the waistband regions 38 and 40, and comprises that portion of the diaper which, when worn, is positioned between the legs of the wearer and covers the lower torso of the wearer. Thus, the intermediate crotch region 42 is an area where repeated fluid surge typically occur in the diaper or other disposable absorbent article.

Backsheet 22 can typically be located along an outer-side surface of the absorbent body 26 and may be composed of a liquid permeable material, but desirably comprises a material which is configured to be substantially impermeable to liquids. For example, a typical backsheet can be manufactured from a thin plastic film, or other flexible liquid-impermeable material. As used in the present specification, the term "flexible" refers to materials which are compliant and which will readily conform to the general shape and contours of the wearers body. Backsheet 22 prevents the exudates contained in absorbent body 26 from wetting articles, such as bedsheets and overgarments, which contact diaper 20. In particular embodiments of the invention, backsheet 22 can include a film, such as a polyethylene film, having a thickness of from about 0.012 millimeters (0.5 mil) to about 0.051 millimeters (2.0 mils). For example, the backsheet film can have a thickness of about 1.25 mil.

Alternative constructions of the backsheet may comprise a woven or nonwoven fibrous web layer which has been totally or partially constructed or treated to impart the desired levels of liquid impermeability to selected regions that are adjacent or proximate the absorbent body. For example, the backsheet may include a gas-permeable, nonwoven fabric layer laminated to a polymer film layer. Other examples of fibrous, cloth-like backsheet materials can comprise a stretch thinned or stretch thermal laminate material composed of a 0.6 mil (0.015 mm) thick polypropylene blown film and a 0.7 ounce per square yard (23.8 gsm) polypropylene spunbond material (2 denier fibers). A material of this type forms the outercover of a HUGGIES® SUPREME diaper, which is commercially available from Kimberly-Clark Corporation. The backsheet 22 typically provides the outer cover of the article. Optionally, however, the article may include a separate outer cover component member which is additional to the backsheet.

Backsheet 22 may alternatively include a micro-porous, "breathable" material which permits gases, such as water vapor, to escape from absorbent body 26 while substantially preventing liquid exudates from passing through the backsheet. For example, the breathable backsheet may be composed of a microporous polymer film or a nonwoven fabric which has been coated or otherwise modified to impart a desired level of liquid impermeability. For example, a suitable microporous film can be a PMP-1 material, which is available from Mitsui Toatsu Chemicals, Inc., a company having offices in Tokyo, Japan; or an XKO-8044 polyolefin film available from 3M Company of Minneapolis, Minn. The backsheet may also be embossed or otherwise provided with a pattern or matte finish to exhibit a more aesthetically pleasing appearance.

In the various configurations of the invention, where a component such as the backsheet 22 or the containment flaps 82 are configured to be permeable to gas while having a resistance and limited permeability to aqueous liquid, the liquid resistant material can have a construction which is capable of supporting a hydrohead of at least about 45 cm of water substantially without leakage therethrough. A suitable technique for determining the resistance of a material to liquid penetration is Federal Test Method Standard FTMS 191 Method 5514, dated Dec. 31, 1968.

The size of the backsheet 22 is typically determined by the size of absorbent body 26 and the particular diaper design selected. Backsheet 22, for example, may have a generally T-shape, a generally I-shape or a modified hourglass shape, and may extend beyond the terminal edges of absorbent body 26 by a selected distance, such as a distance within the range of about 1.3 centimeters to 2.5 centimeters (about 0.5 to 1.0 inch), to provide at least a portion of the side and end margins.

Topsheet 24 presents a body-facing surface which is compliant, soft-feeling, and non-irritating to the wearer's skin. Further, topsheet 24 can be less hydrophilic than absorbent body 26, and is sufficiently porous to be liquid permeable, permitting liquid to readily penetrate through its thickness to reach the absorbent body. A suitable topsheet 24 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. Topsheet 24 is typically employed to help isolate the wearer's skin from liquids held in absorbent body 26.

Various woven and nonwoven fabrics can be used for topsheet 24. For example, the topsheet may be composed of a meltblown or spunbonded web of the desired fibers, and may also be a bonded-carded-web. The various fabrics can be composed of natural fibers, synthetic fibers or combinations thereof.

For the purposes of the present description, the term "nonwoven web" means a web of fibrous material which is formed without the aid of a textile weaving or knitting process. The term "fabrics" is used to refer to all of the woven, knitted and nonwoven fibrous webs.

The topsheet fabrics may be composed of a substantially hydrophobic material, and the hydrophobic material may optionally be treated with a surfactant or otherwise processed to impart a desired level of wettability and hydrophilicity. In a particular embodiment of the invention, topsheet 24 is a nonwoven, spunbond polypropylene fabric composed of about 2.8–3.2 denier fibers formed into a web having a basis weight of about 22 gsm and density of about 0.06 gm/cc. The fabric is surface treated with about 0.28% Triton X-102 surfactant. The surfactant can be applied by any conventional means, such as spraying, printing, brush coating or the like.

The topsheet 24 and backsheet 22 are connected or otherwise associated together in an operable manner. As used herein, the term "associated" encompasses configurations in which topsheet 24 is directly joined to backsheet 22 by affixing topsheet 24 directly to backsheet 22, and configurations wherein topsheet 24 is indirectly joined to backsheet 22 by affixing topsheet 24 to intermediate members which in turn are affixed to backsheet 22. Topsheet 24 and backsheet 22 can, for example, be affixed directly to each other in the diaper periphery by attachment means (not shown) such as adhesive bonds, sonic bonds, thermal bonds, pinning, stitching or any other attachment means known in the art, as well as combinations thereof. For example, a uniform continuous layer of adhesive, a patterned layer of adhesive, a sprayed pattern of adhesive or an array of separate lines, swirls or spots of construction adhesive may be used to affix topsheet 24 to backsheet 22. It should be readily appreciated that the above-described attachment means may also be employed to suitably interconnect and assemble together the various other component parts of the article.

The structure of the absorbent body 26 can include a retention portion, such as the shown an absorbent pad composed of selected hydrophilic fibers and high-absorbency particles, for holding and storing absorbed liquids and other waste materials. The absorbent body is positioned and sandwiched between topsheet 24 and backsheet 22 to form diaper 20. The absorbent body has a construction which is generally compressible, conformable, non-irritating to the wearers skin, and capable of absorbing and retaining body exudates. It should be understood that, for purposes of this invention, the absorbent body structure may comprise a single, integral piece of material, or alternatively, may comprise a plurality of individual separate pieces of material which are operably assembled together.

Various types of wettable, hydrophilic fibrous material can be used to form the component parts of absorbent body 26. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

As used herein, the term "hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with such system, fibers having contact angles less than 90° are designated "wettable", while fibers having contact angles greater than 90° are designated "nonwettable".

The absorbent body structure can comprise a matrix of hydrophilic fibers, such as a web of cellulosic fluff, mixed with particles of high-absorbency material. In particular arrangements, absorbent body 26 may comprise a mixture of superabsorbent hydrogel-forming particles and synthetic polymer meltblown fibers, or a mixture of superabsorbent particles with a fibrous coform material comprising a blend of natural fibers and/or synthetic polymer fibers. The superabsorbent particles may be substantially homogeneously mixed with the hydrophilic fibers, or may be nonuniformly mixed. For example, the concentrations of superabsorbent particles may be arranged in a non-step-wise gradient through a substantial portion of the thickness (z-direction) of the absorbent structure, with lower concentrations toward the bodyside of the absorbent body and relatively higher concentrations toward the outerside of the absorbent structure. Suitable z-gradient configurations are described in U.S. Pat. No. 4,699,823 issued Oct. 13, 1987 to Kellenberger et al., the entire disclosure of which is incorporated herein by reference in a manner that is consistent (not in conflict) with the present description. Alternatively, the concentrations of superabsorbent particles may be arranged in a non-step-wise gradient, through a substantial portion of the thickness (z-direction) of the absorbent structure, with higher concentrations toward the bodyside of the absorbent body and relatively lower concentrations toward the outerside of the absorbent structure. The superabsorbent particles may also be arranged in a generally discrete layer within the matrix of hydrophilic fibers. In addition, two or more different types of superabsorbent may be selectively positioned at different locations within or along the fiber matrix.

The high-absorbency material may comprise absorbent gelling materials, such as superabsorbents. Absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic absorbent gelling material polymers include the alkali metal and ammonium salts of poly (acrylic acid) and poly (methacrylic acid), poly (acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further polymers suitable for use in the absorbent body include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Synthetic absorbent gelling materials typically are xerogels which form hydrogels when wetted. The term "hydrogel", however, has commonly been used to also refer to both the wetted and unwetted forms of the material.

As mentioned previously, the high-absorbency material used in absorbent body 26 is generally in the form of discrete particles. The particles can be of any desired shape, for example, spiral or semi-spiral, cubic, rod-like, polyhedral, etc. Shapes having a large greatest dimension/smallest dimension ratio, like needles, flakes, and fibers, are also contemplated for use herein. Conglomerates of particles of absorbent gelling material may also be used in absorbent body 26. Desired for use are particles having an average size of from about 20 microns to about 1 millimeter. "Particle size" as used herein means the weighted average of the smallest dimension of the individual particles.

The hydrophilic fibers and high-absorbency particles can be configured to form an average composite basis weight which is within the range of about 400–900 gsm. In certain aspects of the invention, the average composite basis weight is within the range of about 500–800 gsm, and preferably is within the range of about 550–750 gsm to provide desired performance.

To improve the containment of the high-absorbency material, absorbent body 26 can include an overwrap, such as wrap sheet 28, which is placed immediately adjacent and around absorbent body 26 and may be bonded to the absorbent structure and to the various other components of the article. The wrap sheet is preferably a layer of absorbent material which covers the major bodyside and outerside surfaces of the absorbent body, and preferably encloses substantially all of the peripheral edges of the absorbent body to form a substantially complete envelope thereabout. Alternatively, the wrap sheet can provide an absorbent wrapping which covers the major bodyside and outerside surfaces of the absorbent body, and encloses substantially only the lateral side edges of the absorbent body. Accordingly, both the linear and the inwardly curved portions of the lateral side edges of the wrap sheet would be closed about the absorbent body. In such an arrangement, however, the end edges of the wrap sheet may not be completely closed around the end edges of the absorbent body at the waistband regions of the article.

For example, the complete wrap sheet 28, or at least the bodyside layer of the wrap sheet, may comprise a meltblown web composed of meltblown fibers, such as meltblown polypropylene fibers. Another example of absorbent wrap 28 may comprise a low porosity cellulosic web, such as a tissue composed of an approximately 50/50 blend of hardwood/softwood fibers.

The absorbent wrap 28 may comprise a multi-element wrapsheet which includes a separate bodyside wrap layer and a separate outerside wrap layer, each of which extends past all or some of the peripheral edges of absorbent body 26. Such a configuration of the wrap sheet can, for example, facilitate the formation of a substantially complete sealing and closure around the peripheral edges of absorbent body 26. In the back waistband portion of the illustrated diaper, the absorbent wrap may also be configured to extend an increased distance away from the periphery of the absorbent body to add opacity and strength to the back sidesections of the diaper. In the illustrated embodiment, the bodyside and outerside layers of absorbent wrap 28 extend at least about ½ inch beyond the peripheral edges of the absorbent body to provide an outwardly protruding, flange-type bonding area over which the periphery of the bodyside portion of the absorbent wrap may be completely or partially connected to the periphery of the outerside portion of the absorbent wrap.

The bodyside and outerside layers of wrap sheet 28 may be composed of substantially the same material, or may be composed of different materials. For example, the outerside layer of the wrap sheet may be composed of a relatively lower basis weight material having a relatively high porosity, such as a wet strength cellulosic tissue composed of softwood pulp. The bodyside layer of the wrap sheet may comprise one of the previously described wrap sheet materials which has a relatively low porosity. The low porosity bodyside layer can better prevent the migration of superabsorbent particles onto the wearer's skin, and the high porosity, lower basis weight outerside layer can help reduce costs.

Diaper 20 can also include a surge management layer 84 which helps to decelerate and diffuse surges of liquid that may be introduced into the absorbent body of the article. In the illustrated embodiment, for example, surge layer 84 can be located on an inwardly facing body side surface of topsheet layer 24. Alternatively, surge layer 84 may be located adjacent to an outer side surface of topsheet 24. Accordingly, the surge layer would then be interposed between topsheet 24 and absorbent body 26. Examples of suitable surge management layers 84 are described in U.S. patent application Ser. No. 206,986 of C. Ellis and D. Bishop, entitled FIBROUS NONWOVEN WEB SURGE LAYER FOR PERSONAL CARE ABSORBENT ARTICLES AND THE LIKE, filed Mar. 4, 1994 (attorney docket No. 11,256); and U.S. patent application Ser. No. 206,069 of C. Ellis and R. Everett, entitled IMPROVED SURGE MANAGEMENT FIBROUS NONWOVEN WEB FOR PERSONAL CARE ABSORBENT ARTICLES AND THE LIKE, filed Mar. 4, 1994 (attorney docket No. 11,387); the entire disclosures of which are hereby incorporated by reference in a manner that is consistent herewith.

Leg elastic members 34 are located in the lateral side margins 110 of diaper 20 and are arranged to draw and hold diaper 20 against the legs of the wearer. The elastic members are secured to diaper 20 in an elastically contractible condition so that in a normal under strain configuration, the elastic members effectively contract against diaper 20. The elastic members can be secured in an elastically contractible condition in at least two ways, for example, the elastic members may be stretched and secured while diaper 20 is in an uncontracted condition. Alternatively, diaper 20 may be contracted, for example, by pleating, and the elastic members secured and connected to diaper 20 while the elastic members are in their relaxed or unstretched condition. Still other mechanisms, such as heat-shrink elastic material, may be used to gather the garment.

In the embodiment illustrated in FIG. 1, leg elastic members 34 extend essentially along the complete length of the intermediate crotch region 42 of diaper 20. Alternatively, elastic members 34 may extend the entire length of diaper 20, or any other length suitable providing the arrangement of elastically contractible lines desired for the particular diaper design.

Elastic members 34 may have any of a multitude of configurations. For example, the width of the individual elastic members 34 may be varied from 0.25 millimeters (0.01 inches) to 25 millimeters (1.0 inches) or more. The elastic members may comprise a single strand of elastic material, or may comprise several parallel or non-parallel strands of elastic material, or may be applied in a rectilinear or curvilinear arrangement. Where the strands are non-parallel, two or more of the strands may intersect or otherwise interconnect within the elastic member. The elastic members may be affixed to the diaper in any of several ways which are known in the art. For example, the elastic members may be ultrasonically bonded, heat and pressure sealed using a variety of bonding patterns, or adhesively bonded to diaper 20 with sprayed or swirled patterns of hotmelt adhesive.

In particular embodiments of the invention, the leg elastic members 34 may include a carrier sheet to which are attached a grouped set of elastics composed of a plurality of individual elastic strands. The elastic strands may intersect or be interconnected, or be entirely separated from each other. The carrier sheet may, for example, comprise a 0.002 cm thick polymer film, such as a film of unembossed polypropylene material. The elastic strands can, for example, be composed of Lycra elastomer available from DuPont, a business having offices in Wilmington, Del. Each elastic strand is typically within the range of about 470–1500 decitex (dtx), and may be about 940–1050 dtx. In particular embodiments of the invention, for example, three or four strands can be employed for each elasticized legband.

In addition, the leg elastics 34 may be generally straight or optionally curved. For example, the curved elastics can be inwardly bowed toward the longitudinal centerline of the diaper. In particular arrangements, the curvature of the elastics may not be configured or positioned symmetrically relative to the lateral centerline of the diaper. The curved elastics may have an inwardly bowed and outwardly bowed, reflex-type of curvature, and the length-wise center of the elastics may optionally be offset by a selected distance toward either the front or rear waistband of the diaper to provide desired fit and appearance. In particular embodiments of the invention, the innermost point (apex) of the set of curved elastics can be offset towards the front or rear waistband of the diaper, and the outwardly bowed reflexed-portion can be positioned toward the diaper front waistband.

As representatively shown, diaper 20 can include a waist elastic 36 positioned in the longitudinal margins of either or both of front waistband 38 and rear waistband 40. The waist elastics may be composed of any suitable elastomeric material, such as an elastomer film, an elastic foam, multiple elastic strands, an elastomeric fabric or the like. For example, suitable elastic waist constructions are described in U.S. Pat. No. 4,916,005 to Lippert et al., the entire disclosure of which is hereby incorporated by reference in a manner that is consistent herewith.

Diaper 20 can also include a pair of elasticized containment flaps 82 which extend generally length-wise along the longitudinal dimension 86 of the diaper. The containment flaps are typically positioned laterally inboard from leg elastics 34, and substantially symmetrically placed on each side of the lengthwise, longitudinal centerline of the diaper. Examples of suitable containment flap constructions are described in U.S. Pat. No. 4,704,116 issued Nov. 3, 1987, to K. Enloe, the entire disclosure of which is hereby incorporated by reference in a manner that is consistent herewith. The containment flaps may be composed of a wettable or a non-wettable material, as desired. In addition, the containment flap material may be substantially liquid-impermeable, may be permeable to only gas or may be permeable to both gas and liquid. Other suitable containment flap configurations are described in U.S. patent application Ser. No. 206,816 of R. Everett et al., filed Mar. 4, 1994 and entitled ABSORBENT ARTICLE HAVING AN IMPROVED SURGE MANAGEMENT (attorney docket No. 11,375), the disclosure of which is hereby incorporated by reference in a manner that is consistent herewith.

In an optional, alternative embodiment of the invention, diaper 20 may include elasticized waist flaps, such as those described in U.S. Pat. No. 4,753,646 issued Jun. 28, 1988, to K. Enloe, the entire disclosure of which is hereby incorporated by reference in a manner that is consistent herewith. Similar to the construction of the containment flaps, the waist flaps may be composed of a wettable or non-wettable material, as desired. The waist flap material may be substantially liquid-impermeable, permeable to only gas, or permeable to both gas and liquid.

To provide a refastenable fastening system, diaper 20 can include an appointed landing zone 78 (FIG. 2), which can provide an operable target area for receiving a releasable attachment of the tape fasteners 44 thereon. In particular embodiments of the invention, the landing zone patch can be positioned on the outward surface of backsheet 22 and is located on the front waistband portion 38 of the diaper. A configuration which employs a releasable, interengaging mechanical fastening system can locate a first portion of the mechanical fastener on the landing zone and a second, cooperating portion of the mechanical fastener on the fastener tab 44. For example, with a hook-and-loop fastener, the hook material 46 can be operably connected to the fastener tabs 44 and the loop material 80 can be operably connected to the landing zone 78. Alternatively, the loop material can be operably connected to the fastener tabs 44 and the hook material can be operably connected to the landing zone.

In the various embodiments of the invention, a tape fastener tab 44 can be located at either or both of lateral end regions 116 and 118 of either or both of waistbands 38 and 40. The representatively shown embodiment, for example, has the fasteners tabs 44 located at the distal side edges of the rear waistband 40.

Figure 4:
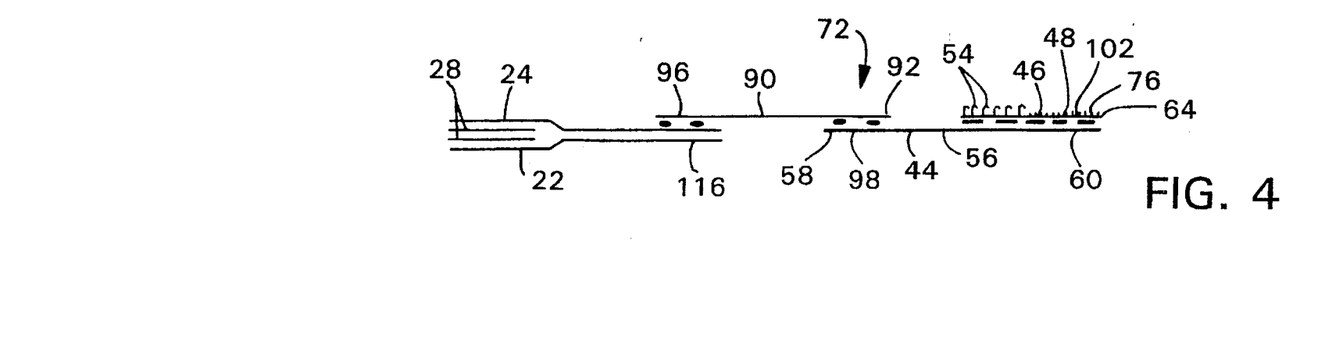
FIG. 4 representatively shows a schematic, laterally extending, expanded edge view of the fastening tab assembly illustrated in FIG. 3.

With reference to FIGS. 1, 3 and 4, each side panel member 90 extends laterally from the opposed lateral ends of at least one waistband portion of backsheet 22, such as the representatively shown rear waistband portion 40, to provide terminal side sections of the article. In addition, each side panel can substantially span from a laterally extending, terminal waistband edge 106 to approximately the location of a corresponding leg opening section of the diaper. Diaper 20, for example, has a laterally opposed pair of leg openings formed by appointed, medial sections of the shown pair of longitudinally extending, side edge regions 110 (FIG. 1 ).

In the various configurations of the invention, the side panels may be integrally formed with a selected diaper component. For example, side panels 90 can be integrally formed from the layer of material which provides backsheet layer 22, or may be integrally formed from the material employed to provide topsheet 24. In alternative configurations, the side panels 90 may be provided by one or more separate members that are connected to backsheet 22, to topsheet 24, in between the backsheet and topsheet, or combinations thereof.

In particular aspects of the invention, each of the side panels 90 may be formed from a separate piece of material which is then suitably assembled and attached to the selected front and/or rear waistband portion of the diaper article. In the illustrated embodiments of the invention, for example, each side panel 90 is attached to the rear waistband portion of backsheet 22 along a side panel attachment zone 96, and can be operably attached to either or both of the backsheet and topsheet components of the article. The side panels extend laterally to form a pair of opposed waist-flap sections of the diaper, and are attached with suitable connecting means, such as adhesive bonding, thermal bonding, ultrasonic bonding, clips, staples, sewing or the like.

The side panels 90 may be composed of a substantially non-elastomeric material, such as polymer films, woven fabrics, nonwoven fabrics or the like, as well as combinations thereof. In particular aspects of the invention, side panels 90 are composed of a substantially elastomeric material, such as a stretch-bonded-laminate (SBL) material, a neck-bonded-laminate (NBL) material, an elastomeric film, an elastomeric foam material, or the like, which is elastomerically stretchable at least along the lateral dimension 88. For example, suitable meltblown elastomeric fibrous webs for forming side panels 90 are described in U.S. Pat. No. 4,663,220 issued May 5, 1987 to T. Wisneski et al., the entire disclosure of which is hereby incorporated by reference. Examples of composite fabrics comprising at least one layer of nonwoven textile fabric secured to a fibrous elastic layer are described in European Patent Application EP No. 0 110 010 published on Apr. 8, 1987 (now EP 0 217 032 A2) which has the listed inventors of J. Taylor et al., the entire disclosure of which is hereby incorporated by reference. Examples of NBL materials are described in U.S. Pat. No. 5,226,992 issued Jul. 13, 1993 to Mormon, the entire disclosure of which is hereby incorporated by reference.

As previously mentioned, various suitable constructions can be employed to attach the side panels 90 to the selected waistband portions of the article. Particular examples of suitable constructions for securing a pair of elastically stretchable members to the lateral, side portions of an article to extend laterally outward beyond the laterally opposed side regions of the outer cover and liner components of an article can be found in U.S. Pat. No. 4,938,753 issued Jul. 3, 1990 to P. VanGompel et al., the entire disclosure of which is hereby incorporated by reference in a manner that is consistent herewith.

Where the side panels 90 are composed of a material which has been elasticized or otherwise constructed to be elastomerically stretchable, the elastomeric side panels can desirably provide an elongation at peak load of at least about 30 percent when subjected to a tensile force load of 0.33 pounds per lineal inch of the sample dimension that is measured perpendicular to the direction of the applied load (about 0.58 Newtons/cm). Alternatively, the elastomeric side panel material can provide an elongation of at least about 100%, and optionally can provide an elongation of at least about 300% to provide improved performance.

Each of the side panels 90 extends laterally from opposed lateral ends of at least one waistband section of the diaper 20. In the shown embodiment, each side panel extends laterally from opposed lateral ends of the rear waistband section of the backsheet 22. With reference to FIGS. 3 and 4, each of the side panels includes a relatively outboard, terminal free end region 92 which has a predetermined length dimension 94 thereof. Each side panel also has a width 91 and a base length 93. The illustrated side panels have a rectangular shape, but may have a tapered or otherwise contoured shape in which the base length 93 is larger or smaller than the relatively outboard free end length 94.

A stress beam section 98 can be constructed on each of the side panels 90 along its outboard, free end region 92 to more evenly distribute tensile stresses across the side panel area. The stress beam section is configured with a relatively high stiffness value, and in desired configurations, the stress beam section extends along substantially the entire longitudinal length of the side panel outboard region 92. A fastening tab 44 can be connected to extend laterally from the stress beam section of each of the side panels 90 for securing the waistband sections of the article about a wearer during the use of the article.

In a particular aspect of the invention, each fastening tab 44 includes a carrier layer 56 which interconnects an inboard edge of the hook member 46 to the outboard edge region of the side panel 90. The carrier layer has a laterally inboard, first side region 58 and a laterally outboard, second side region 60. The first side region 58 is laminated, or otherwise connected and affixed, to the side panel with an operable construction bond. The side panel material, the carrier layer material and the configuration of the construction bond are constructed and arranged to form the operative stress beam section 98. Optionally, an additional layer of reinforcement material may be included along the stress beam region to increase the stiffness of the beam and to further improve its ability to spread stresses along the longitudinal dimension of the side panel. In the arrangement shown in FIG. 3, the inboard region 58 of the carrier layer 56 has a longitudinal extent which is less than the longitudinal dimension 94 of the outboard, free edge portion 92 of the side panel 90. Alternatively, the carrier layer 56 can have a longitudinal extent which is substantially equal to (e.g. FIG. 1) or greater than the longitudinal dimension 94 of the outboard portion of the side panel.

The member of hook material 46 is laminated, or otherwise connected and affixed, to the outboard region of the carrier layer with an operable construction attachment. In particular, the shown hook member 46 is laminated to a inward, bodyside surface of the carrier layer with the hook elements extending generally inwardly of the article. With the illustrated arrangement, the outboard, laterally distal edge of the second carrier edge region 58 is coterminous with the outboard, laterally distal edge of the hook member 46. Alternatively, the outboard, laterally distal edge of the second carrier edge region 58 may be spaced laterally inboard from the terminal, laterally distal edge of the hook member 46. In either configuration, the laterally distal edge of the hook member 46 provides the laterally terminal edge 64 of the article.

The longitudinally extending, relatively outboard edge of the side panel member 90 is spaced from the longitudinally extending, relatively inboard edge of the hook base layer 46 by a carrier spacing distance 61. The outboard edge of the side panel member 90 can also be spaced from the relatively inboard edge of the fastening region 50 by the carrier spacing distance 61. The spacing distance 61 optionally has a lateral extent which is equal to or greater than the lateral extent 69 of the fastening region. In addition, the inwardly facing, bodyside surface of the carrier layer 56 is constructed to have a limited, mechanical interengageability with the hook elements 54. As a result, the fastener tab 44 can be folded along a longitudinally extending fold line to selectively locate and configure the fastening region 50 in a storage position with the hook elements placed and held against the bodyside surface of the carrier layer 56 (FIG. 1).

The level of engagement between the hook material and the carrier layer need only be enough to maintain the storage position. For example, the engagement may provide a peak peel force value within the range of about 1–50 grams of force. Larger levels of peel force may be provided, but such levels can make it more cumbersome to separate and move the hook material away from its storage position into its ordinary, primary fastening position. Where the bodyside surface of the carrier layer is already an exposed woven or nonwoven fabric, the desired engagement can be provided by the ordinary interaction between the fabric matrix and the hook elements. Where the bodyside surface of the carrier layer is not an exposed fabric, the desired engagement can be provided by attaching an operable component of a fabric or other mesh-like material onto the bodyside surface.

In particular configurations of the invention, the material of carrier layer 56 can be composed of a substantially non-elastomeric material, such as polymer films, woven fabrics, nonwoven fabrics or the like, as well as combinations thereof. Alternatively, the carrier web material may be composed of a substantially elastomeric material, such as a stretch-bonded-laminate (SBL) material, a neck-bonded-laminate (NBL) material, an elastomeric film, an elastomeric foam material, or the like, as well as combinations thereof. The elastomeric material is elastomerically stretchable at least along the lateral dimension 88. In the shown arrangement, for example, the carrier web material is composed of a spunbond-meltblown-spunbond (SMS) fabric having a core of meltblown fibers sandwiched between two facing layers of spunbond fibers to provide a total composite basis weight within the range of about 50–67 g/m$^2$ (about 1.5–2 oz/yd$^2$). As another example, the carrier web material may be entirely composed of a nonwoven spunbond fabric having a basis weight within the range of about 50–67 g/m$^2$ (about 1.5–2 oz/yd$^2$).

The mechanical fasteners cooperatively employed with the various configurations of the invention can be provided by mechanical-type fasteners such as hooks, buckles, snaps, buttons and the like, which include cooperating and complementary, mechanically interlocking components. In particular aspects of the invention, the fastening means can be provided by a hook-and-loop fastener system, a mushroom-and-loop fastener system, or the like (collectively referred to as hook-and-loop fasteners). Such fastening systems generally comprise a "hook" or hook-like component, and a cooperating "loop" or loop-like component which engages and releasably interconnects with the hook component. Desirably, the interconnection is selectively releasable. Conventional systems are, for example, available under the VELCRO trademark. Examples of suitable hook-and-loop fastening systems are described in U.S. Pat. No. 5,019,073 issued May 28, 1991 to T. Roessler et al., the entire disclosure of which is hereby incorporated by reference in a manner that is consistent herewith. Other examples of hook-and-loop fastening systems are described in U.S. patent application Ser. No. 366,080 entitled HIGH-PEEL TAB FASTENER, filed Dec. 28, 1994 by G. Zehner et al.; and U.S. patent application Ser. No. 421,640 entitled MULTI-ATTACHMENT FASTENING SYSTEM, filed Apr. 13, 1995 by P. VanGompel et al.; the entire disclosures of which are hereby incorporated by reference in a manner that is consistent herewith.

In a typical configuration of a hook-and-loop fastening system, the hook material member 46 is operably connected to the fastening tab 44, and the loop material 80 is employed to construct at least one cooperating landing zone 78. The landing zone, for example, can be suitably positioned on the exposed, outward-side surface of the backsheet 22. As previously mentioned, an alternative configuration of the hook-and-loop fastening system may have the loop material secured to the fastener tab 44 and may have the hook material employed to form the landing zone 78. In particular aspects of the invention, the hook material member 46 can be of the type referred to as micro-hook material. A suitable micro-hook material is distributed under the designation CS200 and is available from 3M Company, a business having offices in St. Paul, Minn. The micro-hook material can have hooks in the shape of mushroom "caps", and can be configured with a hook density of about 1600 hooks per square inch; a hook height which is within the range of about 0.033–0.097 cm (about 0.013 to 0.038 inch); and a cap width which is within the range of about 0.025–0.033 cm (about 0.01 to 0.013 inch). The hooks are attached to a base film substrate having a thickness of about 0.0076–0.01 cm (about 0.003–0.004 inch) and a Gudey stiffness of about 15 mgf.

Another suitable micro-hook material is distributed under the designation VELCRO CFM-29 1058, and is available from VELCRO U.S.A., Inc., a business having offices in Manchester, N.H. The micro-hook material can have hooks in the shape of angled hook elements, and can be configured with a hook density of about 264 hooks per square centimeter (about 1700 hooks per square inch); a hook height which is within the range of about 0.030–0.063 cm (about 0.012–0.025 inch); and a hook width which is within the range of about 0.007 to 0.022 cm (about 0.003 to 0.009 inch). The hook elements are coextruded with a base layer substrate having a thickness of about 0.0076–0.008 cm (about 0.003–0.0035 inch) and the member of hook material has a Gudey stiffness of about 12 mgf.

In particular aspects of the invention, the longitudinal extent 68 of the fastening region 50 is not more than about 11.4 cm (about 4.5 inch). Alternatively, the longitudinal extent of the fastening region 50 is not more than about 8.9 cm (about 3.5 inch), and optionally is not more than about 6.8 cm (about 2.7 inch) to provide desired levels of performance. In other aspects of the invention, the longitudinal extent 68 of the fastening region 50 is not less than about 2.54 cm (about 1 inch). Alternatively, the longitudinal extent of the fastening region 50 is not less than about 3.3 cm (about 1.3 inch), and optionally is not less than about 4.2 cm (about 1.67 inch) to provide further benefits.

In further aspects, the lateral extent 69 of the fastening region 50 is not more than about 7.6 cm (about 3 inch). Alternatively, the lateral extent of the fastening region 50 is not more than about 3.8 cm (about 1.5 inch), and optionally is not more than about 2.54 cm (about 1 inch) to further provide desired levels of performance. In still other aspects, the lateral extent 69 of the fastening region 50 is not less than about 0.64 cm (about 0.25 inch). Alternatively, the lateral extent of the fastening region 50 is not less than about 0.89 cm (about 0.35 inch), and optionally is not less than about 1.27 cm (about 0.5 inch) to provide further improved performance.

Particular arrangements of the invention can provide the grip region with a lateral extent 62 which is not more than about 25.4 mm (about 1 inch). Alternatively, the lateral extent 62 is not more than about 19 mm (about 0.75 inch), and optionally is not more than about 13 mm (about 0.5 inch) to provided improved benefits. In other aspects, the grip region has a lateral extent 62 which is not less than about 3 mm (about 0.12 inch). Alternatively, the lateral extent 62 is not less than about 4.8 mm (about 0.19 inch), and optionally is not less than about 6 mm (about 0.25 inch) to provide desired performance.

In the shown configuration, substantially the entire area of the grip region 52 of each hook material member 46 is substantially free of hook elements 54. In other aspects of the invention, the grip region can be configured with an appointed region which has a relatively lower density of operative hook elements per unit area, as compared to the fastening region 50.

In another aspect of the invention, the grip region 52 of each member of hook material 46 has a laterally located distal end region 76 which provides for a grip tab 66. The grip tab has a longitudinal extent 70 which is less than a longitudinal extent 68 of its associated fastening region 50 of the hook material member 46. In particular arrangements of the invention, the longitudinal extent 70 of the grip tab 66 is not more than about 80% of the longitudinal extent 68 of its associated fastening region 50. Alternatively, the longitudinal extent of the grip tab 66 is not more about 70%, and optionally is not more than about 60% of the longitudinal extent 68 of its associated fastening region 50 to provide desired levels of performance.

In other arrangements of the invention, the longitudinal extent 70 of the grip tab 66 is not less than about 20% of the longitudinal extent 68 of its associated fastening region 50. Alternatively, the longitudinal extent of the grip tab 66 is not less than about 30%, and optionally is not less than about 40% of the longitudinal extent 68 of its associated fastening region 50 to provide improved performance. In the shown configuration, for example, the longitudinal extent 70 of the grip tab 66 is about 50% of the longitudinal extent 68 of its associated fastening region to provide improved benefits.

The grip region 52, particularly the grip tab 66, is constructed with a relatively high stiffness value to provide improved performance. In particular, the stiffness of the grip region can be configured substantially similar to, or optionally greater than, the stiffness of the fastening region 50. As a result, the grip region can be better maintained in a substantially flat position which is held closely against the landing zone 78. The relative stiffnesses and the high stiffness value can better avoid the presence of a loosely moving flap edge that might be inadvertently pulled to cause a premature pop-open of the fastening system.

In particular aspects, the overall fastener composite formed at the grip region 52, particularly the composite formed at the grip tab 66, has a total stiffness (e.g. a total Gudey stiffness) which is not less than about 80 mgf. Alternatively, the total composite stiffness is not less than about 150 mgf, and optionally is not less about 180 mgf to provided improved performance. Other aspects of the invention can be configured with a total stiffness which is not more than about 250 mgf when measured in the location of the fastener composite formed at the above-mentioned grip region 52 and/or the grip tab 66. Alternatively, the total stiffness is not more than about 225 mgf, and optionally is not more than about 210 mgf to provided improved benefits. The stiffness values are determined with respect to a sample in which the longer, length dimension of the sample corresponds to an alignment along the article cross-dimension 88.

Further aspects of the invention can be configured with the fastener composite at the grip region and/or grip tab having a total stiffness value which is a selected percentage of the total stiffness provided by the fastener composite located at the fastener region 50. In particular, the composite stiffness at the grip region and/or grip tab can be within the range of about 80–120% of the composite stiffness of the fastening region. Alternatively, the grip region and/or grip tab can have a stiffness which is within the range of about 90–110%, and optionally, is within the range of about 95–105% of the composite stiffness of the fastening region.

In further aspects, the stiffness of the grip region can be suitably adjusted by forming a plurality of protrusions 102 (FIGS. 4 and 6) which are distributed over the surface area of the grip region and extend substantially abruptly away from the surface of the base layer 48, and can produce structural discontinuities and stress concentrations in the material of the base layer. The protrusions are configured to be not operatively engageable with the appointed loop material or other second mechanical fastening component. In the representatively shown arrangement, the nonengaging protrusions are distributed in a substantially regularly repeating pattern, and extend approximately perpendicular to the base layer in generally the same direction as the hook elements 54, although alternative non-perpendicular alignments may also be employed. The regular pattern can, for example, be provided by an arrangement of a plurality of rows and/or columns. Optionally, the protrusions can be distributed in a random or other irregular pattern. The representatively shown configuration, for example, has a plurality of protrusions which are integrally formed with the base layer 48 and are composed of substantially the same material as the base layer. It has been found that adding the protrusions 102 can advantageously provide a nonglossy matte finish, and can provide a "dp stop" effect which improves the durability and tear resistance of the hook material. The incorporation of the protrusions can also reduce the stiffness of the grip region 52 to desired levels of stiffness. Desirably, the resultant stiffness of the grip region is less than the stiffness which is exhibited when the grip region lacks the protrusions.

For the purposes of the present invention, the various stiffness values are determined with respect to a bending moment produced by a force which is directed perpendicular to the plane substantially defined by the length and width of the component being tested. A suitable technique for determining the stiffness values described herein is a Gudey Stiffness test, a description of which is set forth in TAPPI Standard Test T 543 om-94 (Bending Resistance of paper (Gudey type tester)). A suitable testing apparatus is a Gudey Digital Stiffness Tester; Model 4171-D manufactured by Teledyne Gudey, a business having offices in Troy, N.Y. This instrument allows the testing of a wide variety of materials through the use of various lengths and widths in combination with the use of a 5, 25, 50, or 200 gram weight placed in one of three positions on the pointer of the apparatus. For purposes of the present description, the stated Gudey stiffness values are intended to correspond to the values that would be generated by a "standard" sized sample. Accordingly, the scale readings from the Gudey stiffness tester are appropriately converted to the stiffness of a standard size sample, and are traditionally reported in terms of milligrams of force (mgf). Currently, a standard "Gudey unit" is equal to a stiffness value of 1 mgf, and may equivalently be employed to report the Gurley stiffness. The standard size sample has a width of 1" and a nominal length of 3" (actual length of 3.5"). The actual length of the sample is the nominal length, plus an additional 0.25" of length for holding in the clamp and another 0.25" of length for overlapping the vane. Tables of factors for taking scale readings generated with non-standard sized test samples and converting the readings to the stiffness of the standard size sample are given in the Instruction Manual for the Gurley Stiffness Tester provided by Teledyne Gudey. Accordingly, other designated dimensions for the test sample may also be conveniently employed, so long as the appropriate conversion factor is employed to determine the appropriate value which corresponds to the standard size sample.

Figure 5:
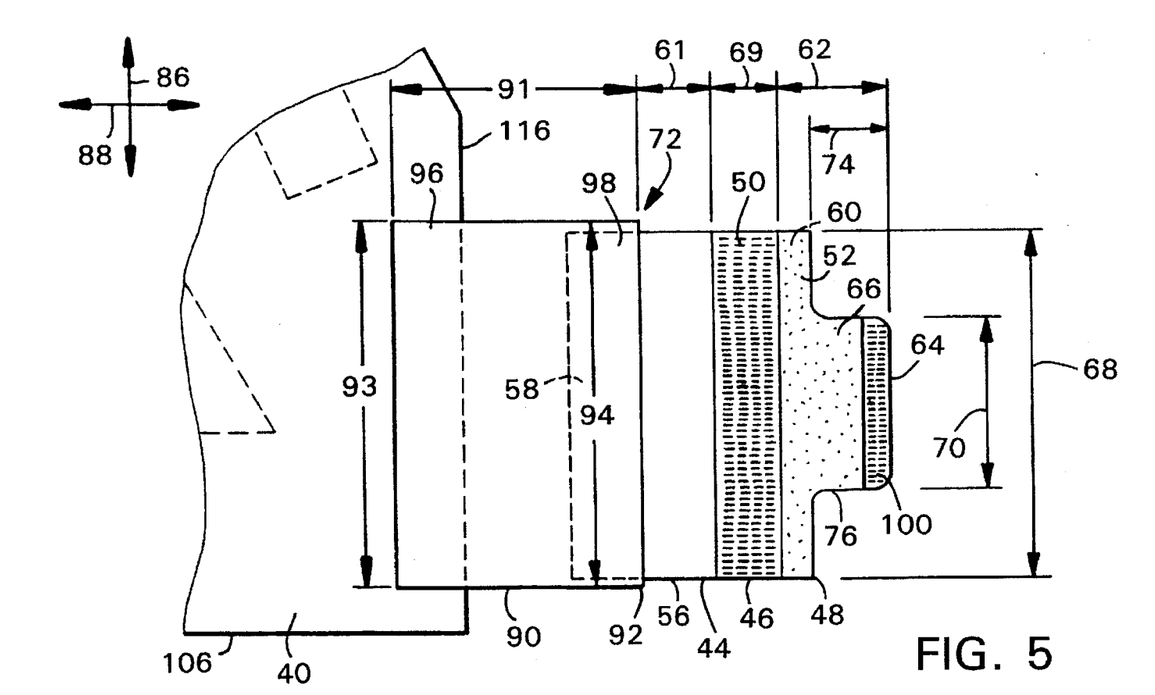
FIG. 5 representatively shows a top view of another side panel and fastening tab assembly having a supplemental fastening region on a grip tab.
Figure 6:
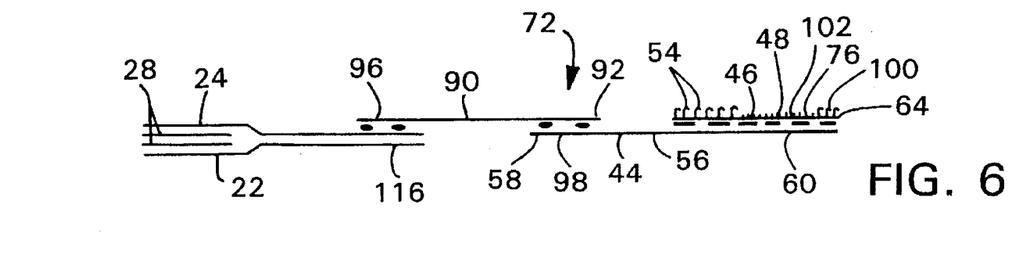
FIG. 6 representatively shows a schematic, laterally extending, expanded edge view of the fastening tab assembly illustrated in FIG. 5.
Figure 7:
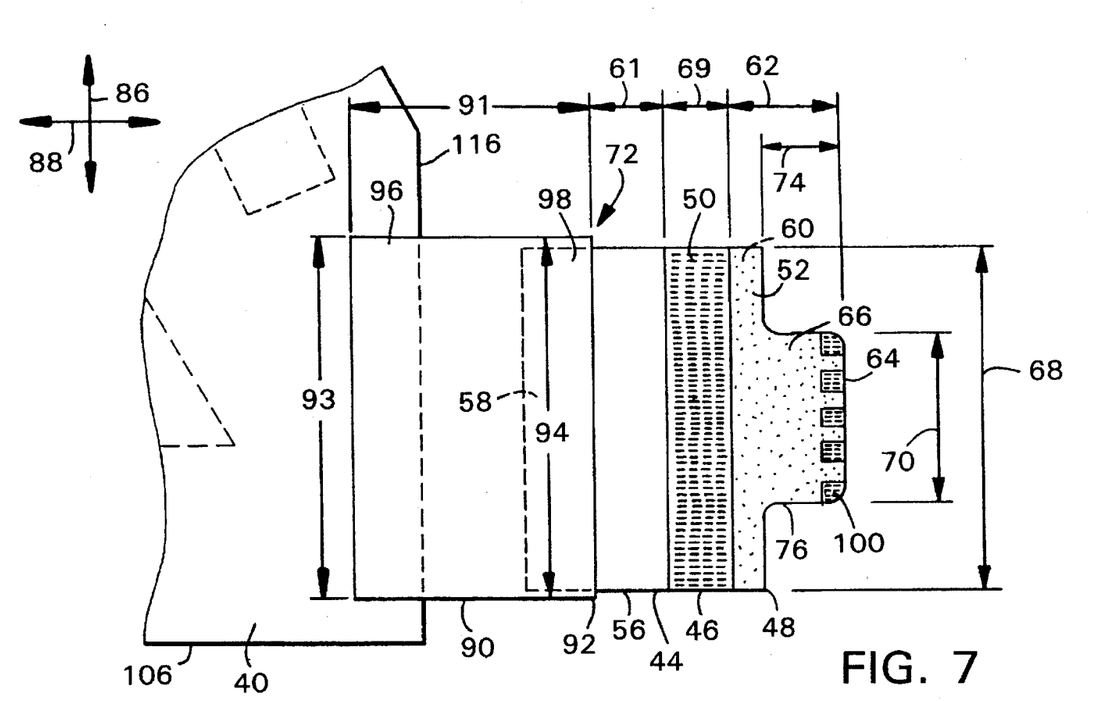
FIG. 7 representatively shows a top view of a side panel and fastening tab assembly having another configuration of the supplemental fastening region on a grip tab.
Figure 8:
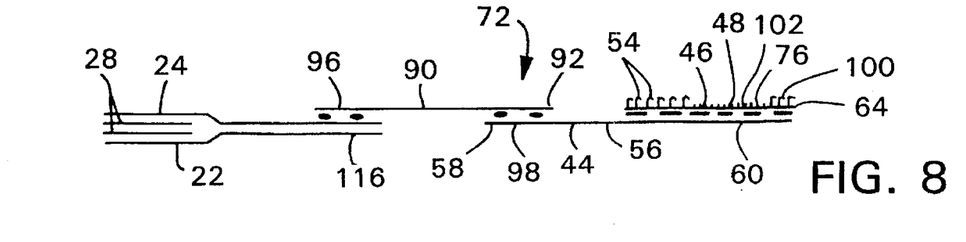
FIG. 8 representatively shows a schematic, laterally extending, expanded edge view of the fastening tab assembly illustrated in FIG. 7.

With reference to FIGS. 5 and 6, a further aspect of the invention can include a grip tab 66 which includes a discrete supplemental fastening region 100 having an area which is less than the total area of the grip region 52 and is separately defined within the grip region. The shown supplemental fastening region is located adjacent to the terminal edge 64 of the grip tab, and is laterally spaced away outboard from the primary fastening region 50. The supplemental fastening region provides for a relatively lower, total fastening strength, as compared to the primary fastening region 50. The lower fastening strength can, for example, be provided for by reducing the effective area of the selected fastening component positioned in the supplemental fastening region, by reducing the density (number or frequency of occurrence) per unit area of the selected fastening elements located in the supplemental fastening region, or by isolating the fastening elements into discrete strip regions or segregated "island" regions. In the representatively shown arrangements, the relatively lower fastening strength is produced by reducing the average hook density in the supplemental fastening region. The average hook element density can, for example, be adjusted by increasing or decreasing the spacing between individual hook elements, or by selectively destroying or otherwise disabling the operable engagability of a selected number of the hook elements. The average hook element density can also be adjusted by limiting the placement of the hook elements into segregated, localized areas. For example, the hook elements may be localized into at least one or more space-apart strip regions which have their major, relatively longer length running substantially along the longitudinal dimension 86 (FIG. 5). Alternatively, the single or plurality of spaced-apart strip regions can have their major lengths aligned to extend laterally, substantially along the article cross-dimension 88. The resultant, cross-directionally aligned strip regions may or may not intersect the pdmary fastening region 50. In still other arrangements, the hook elements may be further localized to create a selected, regular or irregular patchwork pattern having a plurality of segregated, "island" areas, in which the hook-containing island areas are distributed within a "sea" area that is substantially devoid of operable hook elements, as representatively shown in FIGS. 7 and 8.

In particular aspects of the invention, the average hook element density (number or frequency of occurrence) per unit area of the supplemental region 100 can be not more than about 75 percent (%) of the average hook element density within the fastening region 50. Alternatively, the hook element density in the grip region 52 can be not more than about 70%, and optionally can be not more than about 60% of the hook element density within its adjacently located fastening region 50 of the hook material member 46 to provided desired benefits. In further aspects, the average hook element density per unit area of the grip region 52 can be not less than about 10% of the average hook element density within the fastening region 50. Alternatively, the hook element density in the grip region 52 can be not less than about 30%, and optionally can be not less than about 40% of the hook element density within its adjacently located fastening region 50 of the hook material member 46 to provide improved performance.

In other aspects, the supplemental fastening region 100 can be configured substantially coterminous with at least the terminal edge 64 of the grip tab. In other aspects, the supplemental fastening region 100 can be configured substantially coterminous with the periphery of the grip tab, as representatively shown. In further aspects, the laterally outboard, boundary edge of the supplemental fastening region 100 can optionally be spaced laterally inboard from the terminal edge 64 of the grip tab by a selected spacing distance. In other aspects of the invention, the fastening elements in the supplemental fastening region are integrally formed with the base layer.

In the various configurations of the invention, the loop material can be provided by a nonwoven, woven or knit fabric. For example, a suitable loop material fabric can be composed of a 2 bar, warp knit fabric of the type available from Guilford Mills, Inc., Greensborough, N.C. under the trade designation #34285, as well other of knit fabrics. Suitable loop materials are also available from the 3M Company, which has distributed a nylon woven loop under their SCOTCHMATE brand. The 3M Company has also distributed a linerless loop web with adhesive on the backside of the web, and 3M knitted loop tape.

In particular aspects of the invention, the loop material need not be limited to a discrete landing zone patch. Instead the loop material can, for example, be provided by a substantially continuous, outer fibrous layer which is integrated to extend over substantially the total exposed surface area of a cloth-like outer cover employed with the diaper 20. The resultant, cloth-like backsheet 22 can thereby provide the loop material for an operative "fasten anywhere" mechanical fastening system.

The fastening elements in the various constructions of the invention may be operably attached to its base layer by employing any one or more of the attachment mechanisms employed to construct and hold together the various other components of the article of the invention. Desirably, the fastening elements in the various primary and supplemental fastening regions, may be integrally formed, such as by molding, co-extrusion or the like, along with the associated base layer. The base layer and the mechanical fastening elements can be formed from substantially the same polymer material, and there need not be a discrete step of attaching the fastening elements to an initially separate hook base layer. In the representatively shown configurations of the pdmary fastening region 50 and supplemental fastening region 100, for example, the illustrated hook elements 54 are integrally formed along with the hook base layer 48 by coextruding the base layer and hook elements from substantially the same polymer material.

It should be readily appreciated that the strength of the attachment or other interconnection between the base layer and the attached fastening component should be greater than the peak force required to remove the fastener tab 44 from its releasable securement to the appointed landing zone of the article.

Having described the invention in rather full detail, it will be readily apparent that various changes and modifications can be made without departing from the spirit of the invention. All of such changes and modifications are contemplated as being within the scope of the invention as defined by the subjoined claims.

We claim:

1. An article, comprising:
   a side panel having a longitudinal dimension and a lateral dimension;

a first mechanical fastening component operably connected to a first, laterally outboard edge portion of said side panel, said first mechanical fastening component including a base layer which has an appointed fastening region and an appointed grip region, said fastening region having a plurality of first mechanical fastening elements which are integrally formed with said base layer and extend away from a base plane of said base layer, said first mechanical fastening elements configured to operably engage a cooperating, second mechanical fastening component, said grip region having a relatively lower density of said first mechanical fastening elements per unit area, as compared to said fastening region, said fastening region interposed between said side panel and said grip region, said grip region of said base layer of each hook material member including a plurality of non-engaging protrusions extending therefrom, and said grip region of said base layer providing a laterally terminal edge of said article.

2. An article as recited in claim 1, wherein said side panel is elastomerically stretchable.

3. An article as recited in claim 2, wherein said first mechanical fastening component is a member of hook material operably connected to a first, laterally outboard edge portion of said side panel, said member of hook material includes a hook base layer which has an appointed fastening region and an appointed grip region, said fastening region has a plurality of hook elements which are integrally formed with said base layer and extend away from a base plane of said base layer, said hook elements are configured to operably engage a selected, cooperating loop material, said grip region has a relatively lower density of said hook elements per unit area, as compared to said fastening region, said fastening region is interposed between said side panel and said grip region, and said grip region provides a laterally terminal edge of said article.

4. An article as recited in claim 3, wherein said grip region of each hook material member is substantially free of said hook elements.

5. An article as recited in claim 3, wherein said grip region of said member of hook material has a laterally located distal end region, said distal end region including a grip tab which has a longitudinal extent which is less than a longitudinal extent of said fastening region of said hook material member.

6. An article as recited in claim 1, further comprising a carrier layer which includes first and second carrier side regions, and which interconnects between said side panel and said first mechanical fastening component; wherein said first mechanical fasteninq component is affixed to said first carrier side region, and said second carrier side region is attached to said edge portion of said side panel.

7. An article as recited in claim 1, wherein said grip region has a lateral extent of at least about 3 mm.

8. An article as recited in claim 1, said article further comprising: a backsheet layer, a liquid permeable topsheet layer superposed in facing relation with said backsheet layer, and an absorbent body sandwiched between said backsheet layer and topsheet layer; wherein said article has a front waistband section, a rear waistband section and an intermediate section which interconnects said front and rear waistband sections; and said side panel has a second edge portion which is attached to a lateral side region of a one of said waistband sections, said second edge portion positioned laterally opposite to said first edge portion of said side panel.

9. An article as recited in claim 1, wherein said appointed fastening region provides a primary fastening region, and wherein said base layer provides a supplemental fastening region.

10. An article as recited in claim 9, wherein said supplemental fastening region includes a plurality of strip regions of said first mechanical fastening elements, said strip regions having their major lengths extending along said lateral dimension.

11. An article as recited in claim 10, wherein said strip regions of said supplemental fastening region intersect said primary fastening region.

12. An article as recited in claim 9, wherein said supplemental fastening region includes a plurality of discrete islands of said first mechanical fastening elements.

13. An article as recited in claim 9, wherein said supplemental fastening region includes at least one strip region of said first mechanical fastening elements, said strip region having its major length extending substantially along said longitudinal dimension.

14. An absorbent article having a longitudinal dimension, a lateral dimension, a front waistband section with a laterally opposed front pair of side edge regions, a rear waistband section with a laterally opposed rear pair of side edge regions, and an intermediate section which interconnects said front and rear waistband sections, said article comprising:

a backsheet layer;

a liquid permeable topsheet layer superposed in facing relation with said backsheet layer;

an absorbent body sandwiched between said backsheet layer and topsheet layer;

a side panel attached to each of the laterally opposed side edge regions of a one of said waistband sections of said article;

a first fastening component operably connected to a first, laterally outboard edge portion of each side panel, each first fastening component including a base layer which has an appointed fastening region and an appointed grip region, said fastening region having a plurality of first mechanical fastening elements which are integrally formed with said base layer and extend away from a base plane of said base layer, said first mechanical fastening elements configured to operably engage a second mechanical fastening component disposed on an outward surface of the backsheet layer to secure said article on a wearer, said grip region having a relatively lower density of said first mechanical fastening elements per unit area, as compared to said fastening region, said fastening region interposed between said side panel and said grip region, said grip region of said base layer of each hook material member including a plurality of non-engaging protrusions extending therefrom, and said grip region providing a laterally terminal edge of said article.

15. An article as recited in claim 14, wherein said side panel is elastomerically stretchable.

16. An article as recited in claim 15, wherein said first mechanical fastening component is a member of hook material operably connected to a first, laterally outboard edge portion of said side panel, said member of hook material includes a hook base layer which has an appointed fastening region and an appointed grip region, said fastening region has a plurality of hook elements which are integrally formed with said base layer and extend away from a base plane of said base layer, said hook elements are configured to operably engage a selected, cooperating loop material, said grip region has a relatively lower density of said hook elements per unit area, as compared to said fastening region, said fastening region is interposed between said side panel and said grip region, and said grip region provides a laterally terminal edge of said article.

17. An article as recited in claim 16, wherein said grip region of each hook material is substantially free of said hook elements.

18. An article as recited in claim 16, wherein each member of hook material is attached to a carrier layer which interconnects the attached member of hook material to its corresponding side panel; each carrier layer has first and second, laterally opposed side regions; said first side region of each carrier layer is attached to its connected member of hook material; and said second side region of each carrier layer is operably attached to said outboard edge portion of said corresponding side panel.

19. An article as recited in claim 14, wherein said grip region has a lateral extent of at least about 3 mm.

20. An article, comprising:
   a side panel having a longitudinal dimension and a lateral dimension; and
   a fastener which includes a fastener carrier layer, and a first mechanical fastening component attached to said fastener carrier layer; wherein
   said fastener carrier layer includes first and second carrier side regions and interconnects between said side panel and said first mechanical fastening component, said second carrier side region is laminated to a first, laterally outboard edge portion of said side panel, said first mechanical fastening component includes a base layer which is laminated to said first carrier side region and has an appointed fastening region and an appointed grip region, said fastening region of said base layer having a plurality of first mechanical fastening elements which are integrally formed with said base layer and extend away from a base plane of said base layer, said first mechanical fastening elements configured to operably engage a cooperating, second mechanical fastening component, said grip region of said base layer having a relatively lower density of said first mechanical fastening elements per unit area, as compared to said fastening region, said fastening region interposed between said side panel and said grip region, said grip region of of said base layer having a laterally located distal end region with a grip tab, said grip tab having a longitudinal extent which is less than a longitudinal extent of said fastening region of said base layer, and said grip region of said base layer providing a laterally terminal edge of said fastener.

21. An article as recited in claim 20, wherein said side panel is elastomerically stretchable.

22. An article as recited in claim 21, wherein said first mechanical fastening component is a member of hook material, said member of hook material includes a hook base layer which has an appointed fastening region and an appointed grip region, said fastening region has a plurality of hook elements which are integrally formed with said hook base layer and extend away from a base plane of said hook base layer, said hook elements are configured to operably engage a selected, cooperating loop material, said grip region has a relatively lower density of said hook elements per unit area, as compared to said fastening region, said fastening region is interposed between said side panel and said grip region, and said grip region of said hook base layer provides a laterally terminal edge of said fastener.

23. An article as recited in claim 22, wherein said grip region of said hook base layer is substantially free of said hook elements.

24. An article as recited in claim 22, wherein said grip region of said hook base layer of each hook material member includes a plurality of nonengaging protrusions extending therefrom.

25. An article as recited in claim 20, further comprising: a backsheet layer, a liquid permeable topsheet layer superposed in facing relation with said backsheet layer, and an absorbent body sandwiched between said backsheet layer and topsheet layer; wherein said article has a front waistband section, a rear waistband section and an intermediate section which interconnects said front and rear waistband sections; and wherein said side panel includes a second edge portion which has a laminated attachment to a lateral side region of a one of said waistband sections, said second edge portion positioned laterally opposite to said first edge portion of said side panel.

26. An article as recited in claim 20, said article further comprising: a backsheet layer, a liquid permeable topsheet layer superposed in facing relation with said backsheet layer, and an absorbent body sandwiched between said backsheet layer and topsheet layer; wherein said article has a front waistband section, a rear waistband section and an intermediate section which interconnects said front and rear waistband sections; and wherein
   a said side panel is attached to each of the laterally opposed side regions of at least one of said waistband sections, each said side panel including a second edge portion which has a laminated attachment to a lateral side region of a one of said waistband sections, said second edge portion of each side panel positioned laterally opposite to said first edge portion of said each side panel.

27. An article as recited in claim 20, wherein said appointed fastening region provides a primary mechanical fastening region, and wherein said grip region of said base layer includes a separately defined, supplemental mechanical fastening region having a second plurality of said first mechanical fastening elements which are integrally formed with said base layer and extend away from the base plane of said base layer.

28. An article as recited in claim 27, wherein said supplemental fastening region has said second plurality of said first mechanical fastening elements configured to form in a plurality of spaced-apart strip regions, said strip regions having their major lengths extending along said lateral dimension.

29. An article as recited in claim 28, wherein said strip regions of said supplemental fastening region intersect said primary fastening region.

30. An article as recited in claim 29, wherein said supplemental fastening region has said second plurality of said first mechanical fastening elements configured in a plurality of discrete islands.

31. An article as recited in claim 27, wherein said supplemental fastening region has said first mechanical fastening elements arranged in at least one strip region, said strip region spaced away from said primary mechanical fastening region and having its major length extending substantially along said longitudinal dimension.

* * * * *